United States Patent [19]

Yamazaki et al.

[11] Patent Number: 4,820,509

[45] Date of Patent: Apr. 11, 1989

[54] NAIL COSMETIC COMPOSITION

[75] Inventors: Kazunori Yamazaki; Yoshikazu Soyama; Muneo Tanaka; Chigusa Kitamura, all of Yokohama, Japan

[73] Assignee: Shiseido Company Ltd., Tokyo, Japan

[21] Appl. No.: 931,762

[22] Filed: Nov. 17, 1986

Related U.S. Application Data

[63] Continuation of Ser. No. 720,828, Apr. 8, 1985, abandoned.

[30] Foreign Application Priority Data

Apr. 11, 1984 [JP] Japan .................................. 59-72373

[51] Int. Cl.⁴ ............................................. A61K 7/043
[52] U.S. Cl. ...................................... 424/61; 514/844
[58] Field of Search ........................................... 424/61

[56] References Cited

U.S. PATENT DOCUMENTS

| | | | |
|---|---|---|---|
| 3,234,097 | 2/1966 | Loughran et al. | 424/61 |
| 3,864,294 | 2/1975 | Busch, Jr. | 424/61 |
| 3,959,193 | 5/1976 | Putman et al. | 524/563 |
| 4,113,650 | 9/1978 | Putman et al. | 524/39 |
| 4,179,304 | 12/1979 | Rossomando | 424/61 |
| 4,409,203 | 10/1983 | Gordon et al. | 424/61 |

FOREIGN PATENT DOCUMENTS 0154679  9/1985  European Pat. Off. .

Primary Examiner—Ronald W. Griffin
Assistant Examiner—Nancy S. Carson
Attorney, Agent, or Firm—Sprung Horn Kramer & Woods

[57] ABSTRACT

A nail cosmetic composition including 1% to 4% by weight of sucrose benzoate in a nail cosmetic base composed of a sulfon amide resin, nitrocellulose, a plasticizer, and a solvent. This nail cosmetic composition has improved peeling resistance of the coated film thereof without impairing the other desired characteristics.

18 Claims, No Drawings

NAIL COSMETIC COMPOSITION

This is a continuation of application Ser. No. 720,828, filed Apr. 8, 1985, now abandoned.

BACKGROUND OF THE INVENTION

1. Field of the Invention

The present invention relates to a nail cosmetic composition, such as a nail enamel, a nail enamel basecoat, and a nail enamel overcoat, having improved peeling resistance. More specifically, it relates to a solvent-type nail cosmetic composition containing, as a base component, a sulfonamide resin, nitrocellulose, a plasticizer, and a solvent, which is easy to apply to fingernails, is excellent in drying characteristics and glossiness, and is resistant to undesired peeling from the applied films with the elapse of time. By the term "peeling resistance" used herein is meant resistance to chipping, peeling, and abrasion of the coated nail cosmetic films.

2. Description of the Related Art

Recently, solvent-type nail cosmetic compositions have been remarkably improved in quality, especially with the progress made in nitrocellulose lacquers. However, there is still room for improvement in the peeling resistance with the elapse of time.

Of the various characteristics required in nail cosmetic compositions, scratch as the coatability, drying characteristics, gloss, such resistance of the coated film, water resistance, detergent resistance, oil resistance, and peeling resistance (or anti-peeling), various attempts have been made to improve the peeling resistance of the coated film by formulating various resins such as alkyd resins, acrylic resins, modified polyester resins, and sulfonamide resins into nail cosmetic compositions. Of these resins, sulfonamide resins are most preferable to improve the peeling resistance of the coated film. Furthermore, sulfonamide resins are, in general, superior to other resins in various characteristics such as adhesive properties to nails, compatibility with nitrocelluloses, appropriate hardness, flexibility, water resistance, detergent resistance, oil resistance, glossiness, and compatibility with various solvents. For these reasons, sulfonamide resins have become widely used.

However, since nail cosmetic compositions are applied to human nails, they are subjected, after application, to various factors causing the peeling of the coated film, which are derived from various daily actions such as bathing, hair washing, cooking, office work such as typing, and various sports. For these reasons, peeling resistance of the coated films of nail cosmetic compositions containing the above-mentioned sulfonamide resins is still insufficient.

SUMMARY OF THE INVENTION

Accordingly, the objects of the present invention are to eliminate the above-mentioned disadvantage of conventional nail cosmetic compositions and to provide a nail cosmetic composition having improved peeling resistance without impairing the other desired characteristics of the nail cosmetic composition.

Other objects and advantages of the present invention will be apparent from the following description.

In accordance with the present invention, there is provided a nail cosmetic composition comprising 1% to 4% by weight of sucrose benzoate in a nail cosmetic base containing a sulfonamide resin.

DESCRIPTION OF THE PREFERRED EMBODIMENTS

The nitrocelluloses usable as a base component of the nail cosmetic composition in the present invention are those generally used as a film-forming ingredient in conventional nail cosmetic compositions. Examples of such nitrocelluloses are so-called nitrocellulose RS $\frac{1}{2}$ second, nitrocellulose RS $\frac{1}{4}$ second, and nitrocellulose RS $\frac{1}{8}$ second. These introcelluloses can be used alone or in any mixture thereof.

Although there is no critical limitation in the content of the nitrocellulose in the nail cosmetic composition according to the present invention, the nitrocellulose having an isopropyl alcohol (IPA) wetness (or content) of 30% by weight can be, preferably, formulated into the nail cosmetic composition in an amount of 5% to 25% by weight (wet), more preferably 10% to 20% by weight (wet). The use of a too small amount of the nitrocellulose tends to unpreferably result in the coated films to be easily scratched, whereby the glossiness of the coated films is lost with the elapse of time through various daily actions. Contrary to this, the use of a too large amount of the nitrocellulose tends to unpreferably result in the too hard and poor flexible coated films to thereby cause the undesirable peeling of the coated films.

The plasticizers usable as a base component of the nail cosmetic composition in the present invention are those generally used in conventional nail cosmetic compositions. Examples of such plasticizers are phthalate-type plasticizers such as dibutyl phthalate and dioctyl phthalate; citrate-type plasticizers such as tributyl citrate and acetyl tributyl citrate; and camphor. These plasticizers can be used alone or in any mixture thereof.

Although there is no critical limitation in the content of the plasticizer in the present nail cosmetic composition, the plasticizer is preferably formulated into the present nail cosmetic composition in an amount of 2% to 8% by weight, more preferably 4% to 6% by weight. The use of a too small amount of the plasticizer tends to unpreferably result in the too hard and poor flexible coated films to thereby cause the undesirable peeling of the coated film. Contrary to this, the use of a too large amount of the plasticizer tends to unpreferably result in the too flexible coated films to thereby cause the decrease in the glossiness with the elapse of time through various daily actions.

The solvents usable as a base component of the nail cosmetic base in the present invention are those generally used in conventional nail cosmetic compositions. Examples of such solvents are esters such as ethyl acetate, butyl acetate, and amyl acetate; alcohols such as ethyl alcohol, isopropyl alcohol, and butyl alcohol; and hydrocarbon such as toluene. These solvents can be used alone or in any mixture thereof.

Although there is no critical limitation in the content of the solvent in the present nail cosmetic composition, the solvent can be, preferably, formulated into the present nail cosmetic composition in an amount of 60% to 85% by weight, more preferably 70% to 80% by weight. The use of a too small amount of the solvent tends to unpreferably increase the viscosity of the nail cosmetic composition to thereby cause the poor coatability, whereas the use of a too large amount of the solvent tends to unpreferably result in the too thin coated films, when applied, and decrease the glossiness and peeling resistance of the coated films.

The sulfonamide resins usable in the present nail cosmetic composition are those which are known in the art. Typical examples of such sulfonamide resins are toluene sulfonamide/formaldehyde resins (e.g., available from Monsanto Co. under the trademark "Santolite"). The molecular weight of the sulfonamide resin is preferably 1,000 to 10,000 in the practice of the present invention.

Although there is no critical limitation in the content of the sulfonamide resin in the present nail cosmetic composition, the sulfonamide resin can be formulated into the present nail cosmetic composition in an amount of 4% to 12% by weight, preferably 6% to 10% by weight. The use of a too small amount of the sulfonamide resin tends to unpreferably decrease the adhesion of the coated films to nails to thereby cause the poor peeling (or chipping) resistance. Contrary to this, the use of the too large amount of the sulfonamide resin tends to unpreferably result in the too flexible coated films to thereby cause the decrease in the peeling (or abrasion) resistance and the glossiness with the elapse of time through various daily actions. The sucrose benzoate usable in the present invention is commercially available. Examples of such commercially available sucrose benzoates are Monopet SB (trademark, manufactured by Daiichi Kogyo Seiyaku K.K., Japan), and Sucrose Benzoate (manufactured by Velsicol Chemical Corp., USA).

The sucrose benzoate should be formulated into the present nail cosmetic composition in an amount of 1% to 4% by weight, preferably 1.5% to 3% by weight. The use of a too small amount of the sucrose benzoate unpreferably causes insufficient improvement in the peeling resistance of coated film, whereas the use of a too large amount of the sucrose benzoate unpreferably results in the poor peeling resistance of coated film.

The nail cosmetic composition according to the present invention may optionally contain any ingredient generally used in conventional nail cosmetic compositions, as long as the desired objects of the present invention are not adversely affected. Examples of such optional ingredients are pigments such as titanium dioxide, iron oxides lithol rubin BCA, and helindon pint CN; dyes such as sudan III and rhodamine B, pearl essences such as crystalline guanine, bismuth oxychloride, and mica synthetic pearl; gelling agents such as organically modified bentonite; and ultraviolent (UV) absorbers such as 2-hydroxy-4-methoxy benzophenone.

The nail cosmetic composition according to the present invention has excellent peeling resistance in the coated film thereof, in addition to the other characteristics required for nail cosmetic compositions such as easy coatability, drying characteristics, glossiness, and easy removal with a remover.

EXAMPLES

The present invention will now be further illustrated by, but is by no means limited to, the following Examples, wherein "percents" are all by weight unless otherwise specified.

Examples 1 to 5 and Comparative Examples 1 to 7

Red nail cosmetic compositions having the compositions listed in Table 1 were prepared as follows.

The ingredients 9, 10, 11, and 12 were mixed while stirring. To the resultant mixture, the ingredients 7 and 8 and the ingredients 1, 2, 3, 4, and 5 were added and dissolved while stirring. Then, the ingredient 6 was added to the resultant mixture to be dissolved therein while stirring. Finally, the ingredients 13 and 14 were dispersed in the resultant mixture to obtain the red nail cosmetic composition.

TABLE 1

| No. | Ingredient | Example 1 | Example 2 | Example 3 | Example 4 | Example 5 | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|---|---|---|---|
| 1. | Toluene sulfonamide/formaldehyde resin*1 | 8 | 5 | 7 | 7 | 9 | 10 | 8 | — | — | — | 5 | 9 |
| 2. | Sucrose benzoate | 2 | 1 | 2 | 3 | 4 | — | — | 2 | 2 | 2 | 0.5 | 5 |
| 3. | Sucrose acetate isobutylate (SAIB) | — | — | — | — | — | — | 2 | 8 | — | — | — | — |
| 4. | Acrylic resin*2 | — | — | — | — | — | — | — | — | 8 | — | — | — |
| 5. | Alkyd resin*3 | — | — | — | — | — | — | — | — | — | 8 | — | — |
| 6. | Nitrocellulose RS ¼ second (30% IPA) | 15 | 15 | 15 | 15 | 15 | 15 | 15 | 15 | 15 | 15 | 15 | 15 |
| 7. | dibutyl phthalate | 4 | 4 | 4 | 4 | 4 | 4 | 4 | 4 | 4 | 4 | 4 | 4 |
| 8. | Camphor | 2 | 2 | 2 | 2 | 2 | 2 | 2 | 2 | 2 | 2 | 2 | 2 |
| 9. | Ethyl acetate | 10 | 10 | 10 | 10 | 10 | 10 | 10 | 10 | 10 | 10 | 10 | 10 |
| 10. | n-Butyl acetate | 30 | 34 | 31 | 30 | 27 | 30 | 30 | 30 | 30 | 30 | 34.5 | 26 |
| 11. | Isopropyl alcohol | 7 | 7 | 7 | 7 | 7 | 7 | 7 | 7 | 7 | 7 | 7 | 7 |
| 12. | Toluene | 20 | 20 | 20 | 20 | 20 | 20 | 20 | 20 | 20 | 20 | 20 | 20 |
| 13. | Pigment (lithol rubin BCA/TiO$_2$ = 4/1) | 1 | 1 | 1 | 1 | 1 | 1 | 1 | 1 | 1 | 1 | 1 | 1 |
| 14. | Organically modified bentonite gelling agent*4 | 1 | 1 | 1 | 1 | 1 | 1 | 1 | 1 | 1 | 1 | 1 | 1 |

*1 Santolite MHP (Monsanto Co.)
*2 n-Butyl acrylate/Methyl methacrylate copolymer (M.W. = about 4000)
*3 Modified glycidyl ester of Versatic 911 (M.W. = about 20,000)
*4 Bentone 27 (available from National Lead Co., USA)

The nail cosmetic compositions prepared in Examples 1 to 5 and Comparative Examples 1 to 7 were evaluated in respect of the coatability, drying characteristics, glossiness, hardness (i.e., scratch resistance of the coated film), flexibility of the coated film, and peeling resistance of the coated film.

The evaluation methods were as follows.

Coatability

The sample was filled in a glass container provided with an application brush and the coatability was visually evaluated in twice coating according to the following criteria.

+: Good (i.e., Easy to coat with clean and smooth coating)
±: Fair (i.e., Somewhat difficult to coat)
−: Poor (i.e., Very difficult to coat)

Drying characteristics

Nails were coated twice with the sample composition in a room at 25° C. and, thereafter, a drying rate to dry to the touch was determined. The results were evaluated according to the following criteria.
+: Drying rate of 2 to 5 minutes
±: Drying rate of 5 to 8 minutes
−: Drying rate of more than 8 minutes Glossiness The sample composition was uniformly coated on a glass plate with a 0.35 mm doctor blade and was dried at room temperature for 24 hours. The gloss of the coated film was measured at an inclination angle of 60° and a reflection angle of 60° by means of D-2 type glossmeter (manufactured by Nippon Denshoku Kogyo Co., Ltd., Japan). The evaluation was carried out according to the following criteria.
+: gloss of 90 to 100
±: gloss of 70 to 90
−: gloss of less than 70

Hardness (scratch resistance of coated film)

The sample composition was uniformly coated on a glass plate with a 0.35 mm doctor blade and was dried at room temperature for 48 hours. The hardness of the resultant coated film was determined with a Vickers hardness tester under a load of 25 g for 5 seconds. The hardness of the coated film was evaluated from the measured data according to the following criteria. The coated film is soft and easy to scratch when the data is large.
+: hardness of 70 to 100
±: hardness of 100 to 130
−: hardness of 130 to 160

Flexibility of Coated Film

The sample composition was uniformly coated on a polyvinyl chloride plate with a 0.85 mm doctor blade and the resultant uniform coated film was dried at room temperature for 48 hours. The dried film had a size of 10 mm × 60 mm and a thickness of about 60 μm. The elongation at breakage was determined at a stress rate of 20 mm/min by a tensile tester. The evaluation was carried out as follows.
+: Elongation at breakage of 15% to 25% (Moderate flexibility)
±: Elongation at breakage of 25% to 35% (Excessive flexibility)
−: Elongation at breakage of less than 15% (No flexibility)

Peeling Resistance

The sample composition was uniformly coated on a nylon plate with a 0.35 mm doctor blade, and the resultant film was dried at room temperature for 24 hours. The dried film was evaluated by a cross-cut test. Thus, the film was longitudinally and latitudinally cut to form 100 squares each having a size of 1 mm × 1 mm. The results were determined as follows.
+: Regular squares were formed by cutting.
±: Squares were somewhat distorted after cutting.
−: Squares were formed in jagged shapes after cutting.

Furthermore, the peeling resistance of the sample compositions were organoleptically evaluated for each sample by using a panel composed of 10 female members. The sample was coated on the 100 fingernails of the 10 women and left for 3 days. After 3 days, the length of the film peeling from the tip of the fingernails was measured. The results were averaged and evaluated according to the following criteria based on the average peeling length per one fingernail.
+: Peeling length of 0.5 to 1.0 mm
±: Peeling length of 1.0 to 1.5 mm
−: Peeling length of more than 1.5 mm The evaluation results were as shown in Table 2.

TABLE 2

| Evaluation item | Example | | | | | Comparative example | | | | | | |
|---|---|---|---|---|---|---|---|---|---|---|---|---|
| | 1 | 2 | 3 | 4 | 5 | 1 | 2 | 3 | 4 | 5 | 6 | 7 |
| Coatability | + | + | + | + | + | + | + | + | + | ± | + | ± |
| Drying characteristics | + | + | + | + | + | + | + | + | + | + | + | + |
| Gloss of coated film | + | + | + | + | + | + | + | + | ± | ± | + | + |
| Hardness of coated film | + | + | + | + | + | ± | ± | ± | ± | ± | ± | + |
| Flexibility of coated film | + | + | + | + | + | ± | ± | ± | ± | − | ± | − |
| Peeling resistance (Cross-cut test) | + | + | + | + | + | ± | ± | ± | − | − | ± | ± |
| (Application test) | + | + | + | + | + | ± | ± | ± | − | − | ± | ± |
| Overall evaluation result | + | + | + | + | + | ± | ± | ± | − | − | ± | ± |

As is clear from the results shown in Table 2, the nail cosmetic compositions of Examples 1 to 5 containing both the sulfonamide and the sucrose benzoate exhibited excellent results in each evaluation test of the coatability to nails, drying characteristics, glossiness of the coated film, hardness of the coated film (scratch resistance), flexibility of the coated film, and peeling resistance of the coated film (cross-cut test and actual application test) and, therefore, the overall evaluation results were excellent.

Contrary to the above, the nail cosmetic compositions of Comparative Examples 1 to 7 did not exhibit the desired results. That is, the nail cosmetic composition of Comparative Example 1 containing the sulfonamide resin but not containing sucrose benzoate did not exhibit the desired results in the hardness of the coated film, the scratch resistance of the coated film, and the peeling resistance of the coated film.

The nail cosmetic composition of Comparative Example 2, in which the sulfonamide resin was used in combination with the sucrose acetate isobutyrate, did not exhibit the desired results as in Comparative Example 1. Thus, the combined use of the sulfonamide resin with the sucrose acetate isobutyrate cannot improve the peeling resistance of the coated film.

The nail cosmetic composition of Comparative Example 3, in which the sucrose benzoate was used in combination with sucrose acetate isobutyrate, did not exhibit the desired results as in Comparative Example 1.

The nail cosmetic composition of Comparative Example 4 containing the sucrose benzoate in combination with an acrylic resin exhibited poor results, especially in the peeling resistance of the coated film.

The nail cosmetic composition of comparative Example 5 containing the sucrose benzoate in combination with an alkyd resin also exhibited poor results, especially, in the peeling resistance as in Comparative Example 4.

The nail cosmetic composition of Comparative Example 6 containing the sulfonamide resin with a too small amount of the sucrose benzoate did not sufficiently improve the peeling resistance of the coated film unlike the nail cosmetic compositions of Examples 1 to 5.

The nail cosmetic composition of Comparative Example 7 containing the sulfonamide resin with a too large amount of the sucrose benzoate exhibited poor flexibility of the coated film and insufficient peeling resistance of the coated film.

As illustrated in the above-mentioned examples, the solvent-type nail cosmetic compositions according to the present invention have excellent peeling resistance of the coated film as well as excellent easy coatability of nails, drying characteristics of the coated film, and hardness of the coated film (i.e., scratch resistance). Thus, it has been confirmed that the present nail cosmetic composition advantageously satisfies the characteristics required for the desirable nail cosmetic composition.

We claim:

1. A nail cosmetic composition comprising 1% to 4% by weight of sucrose benzoate in a nail cosmetic base containing 4 to 12% by weight of a sulfonamide resin, nail coatings made therefrom exhibiting improved peeling resistance.

2. A nail cosmetic composition as claimed in claim 1, wherein the content of the sucrose benzoate is 1.5% to 3% by weight in the composition.

3. A nail cosmetic composition as claimed in claim 1, wherein the nail cosmetic base is composed of 5% to 25% by weight of nitrocellulose, 2% to 8% by weight of a plasticizer, 60% to 85% by weight of a solvent, and 4% to 12% by weight of the sulfonamide resin, all based on the weight of the composition.

4. A nail cosmetic composition according to claim 3, wherein the nitrocellulose is selected from the group consisting of nitrocellulose RS ½ second, nitrocellulose RS ¼ second, nitrocellulose RS ⅛ second and mixtures thereof.

5. A nail cosmetic composition according to claim 3, wherein the nitrocellulose has an isopropyl alcohol wetness of 30% by weight.

6. A nail composition according to claim 3, wherein the nitrocellulose is contained in an amount of 10 to 20% by weight.

7. The nail cosmetic composition according to claim 3, wherein the plasticizer is selected from the group consisting of a phthalate, a citrate, camphor and mixtures thereof.

8. A nail cosmetic composition according to claim 7, wherein the phthalate is selected from the group consisting of dibutyl phthalate and dioctyl phthalate.

9. A nail cosmetic composition according to claim 7, wherein the citrate is selected from the group consisting of tributyl citrate and acetyl tributyl citrate.

10. A nail cosmetic composition according to claim 3, wherein the plasticizer is contained in an amount of 4% to 6% by weight.

11. A nail cosmetic composition according to claim 3, wherein said solvent is selected from the group consisting of esters, alcohols and hydrocarbons.

12. A nail cosmetic composition according to claim 3, wherein the solvent is contained in an amount of 70% to 80% by weight.

13. A nail cosmetic composition according to claim 11, wherein said ester is selected from the group consisting of ethyl acetate, butyl acetate and amyl acetate.

14. A nail cosmetic composition according to claim 11, wherein said alcohol is selected from the group consisting of ethyl alcohol, isopropyl alcohol and butyl alcohol.

15. A nail cosmetic composition according to claim 11, wherein said hydrocarbon is toluene.

16. A nail cosmetic composition according to claim 3, wherein the sulfonamide resin is contained in an amount of 6% to 10% by weight.

17. A nail cosmetic composition according to claim 3 wherein the sulfonamide resin has a molecular weight of 1,000 to 10,000.

18. A nail cosmetic composition according to claim 3, wherein the resin is a toluene sulfonamide/formaldehyde resin.

* * * * *